(12) United States Patent  (10) Patent No.: US 7,784,355 B2
Kawano  (45) Date of Patent: Aug. 31, 2010

(54) MATERIAL TESTING MACHINE

(75) Inventor: Toshiyuki Kawano, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 98 days.

(21) Appl. No.: 12/163,348

(22) Filed: Jun. 27, 2008

(65) Prior Publication Data

US 2009/0007689 A1  Jan. 8, 2009

(30) Foreign Application Priority Data

Jul. 4, 2007  (JP) .............................. 2007-176437

(51) Int. Cl.
*G01N 3/00* (2006.01)
(52) U.S. Cl. .............................. 73/788; 73/760; 73/856
(58) Field of Classification Search ........... 73/760–788, 73/856
See application file for complete search history.

(56) References Cited

U.S. PATENT DOCUMENTS 4,096,741 A * 6/1978 Sternstein .................... 73/817
6,718,820 B2 * 4/2004 Kwon et al. .................... 73/81
7,313,971 B2 * 1/2008 Kawano ........................ 73/794

FOREIGN PATENT DOCUMENTS

JP  2002-365188  12/2002

* cited by examiner

*Primary Examiner*—Max Noori
(74) *Attorney, Agent, or Firm*—J.C. Patents

(57) ABSTRACT

A material testing machine is provided, in which a motor is used as a driving source of a loading mechanism, and the material testing machine can always perform a material test accurately, without requiring skilled operators, trial and error, or a longer time when setting control gains. A ratio $K(t)$ of an inspection value $F(t)$ of a control quantity to a displacement $\theta(t)$ of a motor 21 is calculated sequentially, and a value proportional to a value obtained by dividing a deviation $\{F_D(t) - F(t)\}$ by the calculated ratio $K(t)$ is taken as a rotation angle command and supplied to a servo amplifier 36. The servo amplifier 36 supplies a current to the motor 21. Therefore, as the test proceeds, appropriate gains are automatically calculated and set, a gain setting operation before test is not necessary, and the material test can be always performed accurately.

4 Claims, 2 Drawing Sheets

MATERIAL TESTING MACHINE

CROSS-REFERENCE TO RELATED APPLICATION

This application claims the priority benefit of Japan application serial no. JP2007-176437, filed Jul. 4, 2007. All disclosure of the Japan application is incorporated herein by reference.

BACKGROUND OF THE INVENTION

1. Field of the Invention

The present invention generally relates to a material testing machine, in particular, to a material testing mechanism using a motor as a driving source of a loading mechanism.

2. Description of Related Art

A material testing machine using a motor as a driving source of a loading mechanism usually adopts the following structure, that is, two screw rods are supported on a table in this manner of being rotated freely, and two ends of a cross head are supported on each screw rod by means of nuts. The material testing mechanism is configured through the following manner, that is, each screw rod is made to rotate as the motor rotates, so as to make the cross head move, thereby applying a load to a test piece, and at this time, two ends of the test piece are held by chucks installed on the cross head and the table respectively.

In the material testing machine, a servomotor is generally used as the motor for driving the loading mechanism, and a test force applied to the test piece or an elongation of the test piece or the like is selected as a control quantity, and an instant inspection value of a physical quantity of the control quality is fed back to a target value, so as to control the motor (for example, with reference to Patent Document 1).

For example, under a situation of selecting the test force as the control quantity, a proportional integration differential (PID) and other operations are performed on the deviation between the inspection value (current value) and the target value, and a value corresponding to the result of the above operation is taken as a rotation angle command and sent to a servo amplifier, which supplies a driving signal to the motor used for driving, so as to control the motor.

Particularly, the rotation angle command is determined by combining constant times (proportional gain) of the deviation, constant times (derivative gain) of the time differential of the deviation, with constant times (integral gain) of the time integration of the deviation.

[Patent Document 1] Japanese Patent Laid-Open Publication NO. 2002-365188

However, in the material testing machine using the motor as the driving source of the loading mechanism, although the material test for tracking accurate target values can be performed accurately by appropriately setting the proportional gain, derivative gain, and integral gain, generally, in the system (sometimes including the test piece) each gain is actually set through trial and error.

Therefore, especially when testing a new type of test pieces, not only the corresponding time is required, but also skilled operators are required when each gain is set. However, it still cannot ensure that the test is performed accurately.

SUMMARY OF THE INVENTION

The present invention is completed in view of the above practical situations, and the present invention is directed to a material testing machine, which uses a motor as a driving source of a loading mechanism, without requiring skilled operator, trial and error, or a longer time when control gains are set, and it can always perform a material test accurately.

In order to achieve the above object, a material testing machine is provided in the present invention, in which the motor is used as the driving source of the loading mechanism that applies a load to a test piece. The material testing machine includes a control mechanism. The control mechanism sends instantly a rotation angular velocity command of the motor to a servo amplifier that drives the motor, so as to control actions of the loading mechanism. According to a deviation between an inspection value and a target value of a selected control quantity, the control mechanism calculates a rotation angular velocity supplied to the servo amplifier as a command. As for the material testing machine, the control mechanism calculates sequentially a ratio of the inspection value of the control quantity to a displacement of the motor, and takes a value proportional to a value obtained by dividing the deviation by the calculated ratio to serve as the rotation angular velocity, in which the rotation angular velocity is supplied to the servo amplifier as the command (Claim 1).

In the present invention, the following structure may be preferably adopted, that is, the displacement of the motor and the inspection value used to calculate the ratio are respectively an average value of a plurality of latest displacements of the motor and an average value of a plurality of latest inspection values obtained at a time point at which the ratio is calculated (Claim 2).

Furthermore, the following structure may be adopted, that is, the rotation angle supplied to the servo amplifier is obtained by multiplying a value obtained by dividing the deviation by the ratio with an inverse of a preset time constant (Claim 3).

The present invention has the following efficacies. The displacement of the motor is made to be θ(t), the inspection value (current value) of the control quantity, for example, test force, is made to be F(t), and the variance ratio K(t) represented by the following equation is calculated instantly.

[Equation 1]

$$K(t) = \frac{F(t) - F(t - t_0)}{\theta(t) - \theta(t - t_0)}. \quad (1)$$

In [Equation 1], the motor displacement θ(t-t₀) and F(t-t₀) at the time moment t-t₀ are used, in which the time moment t-t₀ is a certain time later since the time point t. Then, a value proportional to a value obtained by dividing the deviation by the variance ratio K(t) is taken as the rotation angular velocity dΘ/dt supplied to the servo amplifier. If the dΘ)/dt is indicated by an equation, the current inspection value of the control quantity is made to be F(t), the target value of the control quantity at this time point is made to be $F_D(t)$, and the deviation is made to be {$F_D(t)$−F(t)}, so as to obtain the following [Equation 2].

[Equation 2]

$$\frac{d\Theta(t)}{dt} = \frac{A}{K(t)}\{F_D(t) - F(t)\}. \quad (2)$$

In Equation (2), A is a preset constant, which is equal to the inverse of the time constant (time constant of the variance of the deviation) in Claim 3. If it intends to quickly converge the deviation, A may be increased, and if it intends to slowly converge the deviation, A may be reduced.

According to the present invention, the ratio of the instant rotation angular velocity command dΘ/dt supplied to the amplifier of the motor driving the loading mechanism to the deviation is automatically determined according to the ratio of the inspection value variation of the control quantity to the variation of the motor displacement, and is controlled in the following manner. When the ratio of the inspection value variation of the control quantity to the variation of the motor displacement is increased, the ratio is reduced, and when the ratio of the inspection value variation of the control quantity to the variation of the motor displacement is reduced, the ratio is increased. In other words, if the ratio is larger, the proportional gain is set to be smaller; and if the ratio is smaller, the proportional gain is automatically set to be larger. In this manner, it can always perform the material test accurately, without necessarily setting the gains by trail and error before the test.

The following situations are taken as preconditions of the present invention, that is, the control quantity is approximately proportional to the rotation angle of the motor momentarily. As the test proceeds, plastic deformation occurs to the test piece, such that the proportional constant varies.

That is, the initial motor displacement when the test begins is made to be θ(t), the inspection value of, for example, test force selected as the control quantity is made to be F(t), so as to obtain the following [Equation 3].

[Equation 3]

$$F(t) - F_R(t) = K(t) \times \theta(t) \quad (3).$$

The Equation 3 is used to indicate the following situation, that is, the test force F(t) serviced as the control quantity is proportional to the motor displacement (rotation angle) θ(t). Since $F_R(t)$ varies as time elapsed, strictly speaking, it is not in a proportional relation. Those other than the proportional items are represented by $F_R(t)$. Such relation is demonstrated by a diagram as shown in FIG. 2, in which X axis indicates the motor displacement (the initial rotation angle is made to be 0 when the test begins) θ, and Y axis indicates the inspection value of the test force F(t) serviced as the control quantity.

The time differential is performed on the two sides of Equation 3, so as to obtain the following [Equation 4].

[Equation 4]

$$\frac{dF(t)}{dt} - \frac{dF_R(t)}{dt} = K(t)\frac{d\theta(t)}{dt} + \frac{dK(t)}{dt}\theta(t). \quad (4)$$

Here, generally, $dF_R(t)/dt$ is not 0, but a parameter with the following features, in which the characteristics of the test piece are changed as the test proceeds, such that the parameter varies as the time elapses. Generally, the characteristics of the material are changed slowly, and the time variance $dF_R(t)/dt$ is quite a small value, so that $dF_R(t)/dt$ can be treated to be 0, i.e., $dF_R(t)/dt=0$.

Similarly, although the ratio K(t) also varies as the time elapses, the variation is rather small, and if dK(t)/dt=0, the following [Equation 5] is obtained.

[Equation 5]

$$\frac{dF(t)}{dt} = K(t) \times \frac{d\theta(t)}{dt} \quad (5)$$

Here, when the rotation angular velocity dΘ/dt of the motor is used as a control input, i.e., an operating quantity relative to the servo amplifier, the actual rotation angular velocity dθ/dt of the motor relies on the load of the motor, and is not totally equal to the rotation angular velocity command dΘ/dt supplied to the servo amplifier, but generally, under the situation of using the servomotor, it is quite close to that under the situation of using the servo amplifier.

Therefore, Equation (5) is approximated by the following Equation (6).

[Equation 6]

$$\frac{dF(t)}{dt} = K(t) \times \frac{d\Theta}{dt}. \quad (6)$$

Furthermore, K(t) varies as the test proceeds, so that the instant inspection value of the control quantity and the motor displacement are used to calculate K(t) instantly, and then, through Equation (2), the calculated K(t) and the deviation at this time point are used to calculate the angular velocity command of the motor supplied to the servo amplifier.

If the Equation (2) is substituted in Equation (6), the following [Equation 7] is obtained.

[Equation 7]

$$\frac{dF(t)}{dt} = A\{F_D(t) - F(t)\}. \quad (7)$$

If

[Equation 8]

$$E = F(t) - F_D(t) \quad (8),$$

the following Equation 9 is obtained.

[Equation 9]

$$\frac{dF(t)}{dt} = -AE. \quad (9)$$

In Equation 9, A represents a time constant of the error variation, which may be determined by considering the expected time constants. For example, when A=1, as for the time variation of the error with respect to the step response, if "the target time differential $dF_D/dt$ of the step response is 0" is considered, the following [Equation 10] is obtained.

[Equation 10]

$$E = \exp(-t) \quad (10).$$

Therefore, the error after one second can be calculated as exp(−1)=0.36.

EFFECT OF INVENTION

According to the present invention, as for the material testing machine using the motor as the driving source of the loading mechanism, it is not necessary to set the gains that are used for performing a feedback control on the motor. According to the instant motor displacement (rotation quantity) and the inspection value of the control quantity, the instant appropriate gains can be automatically calculated and successively set.

Therefore, before the test, the operators do not need to set the gains by trial and error as in a prior art, so that the time is saved, the skilled operators are not required, and the present invention can always perform the material test accurately.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
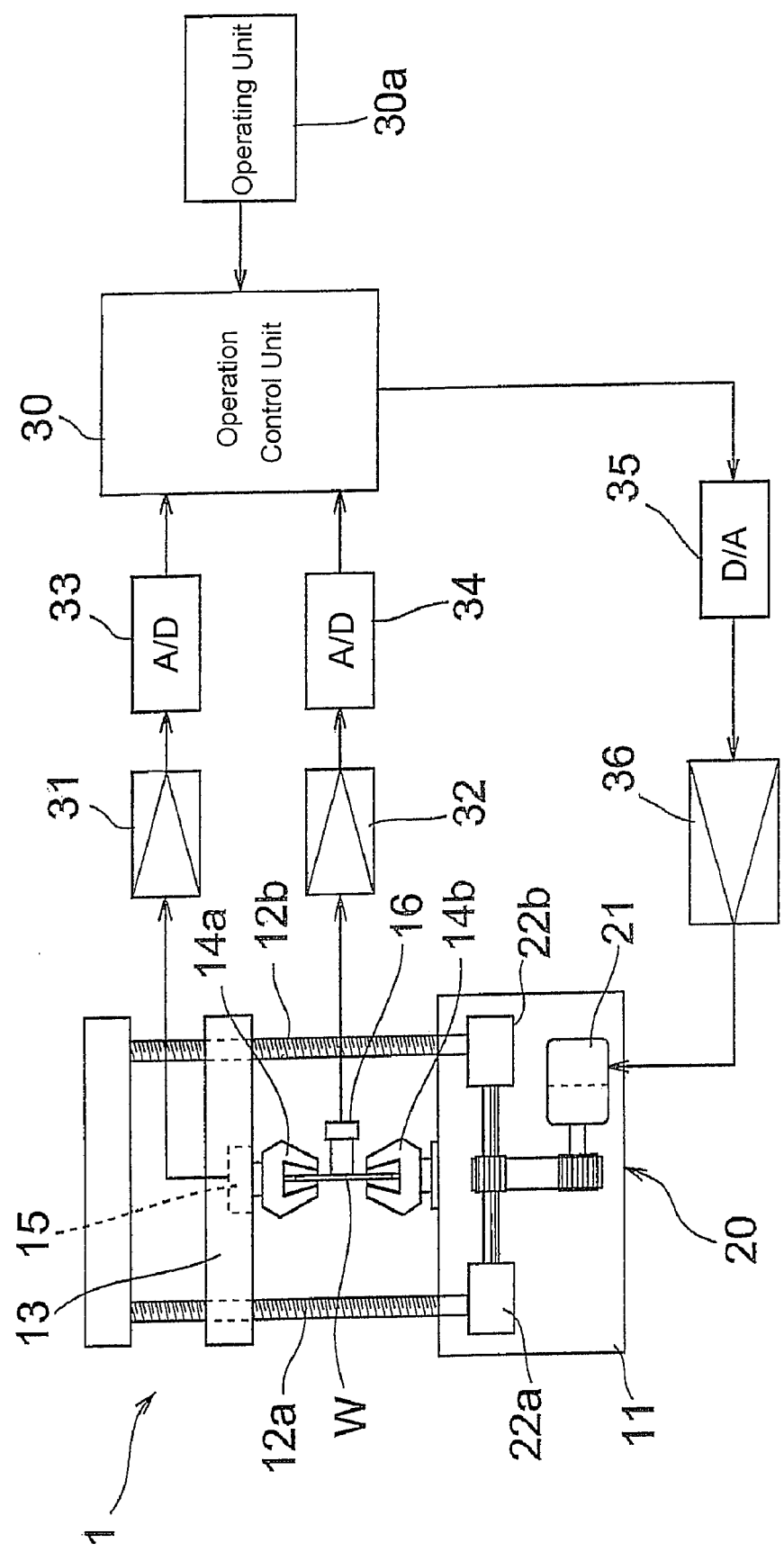
FIG. 1 is a structural view of an embodiment of the present invention, a schematic view showing a mechanical configuration, and a block diagram showing an electrical configuration of the present invention.
Figure 2:
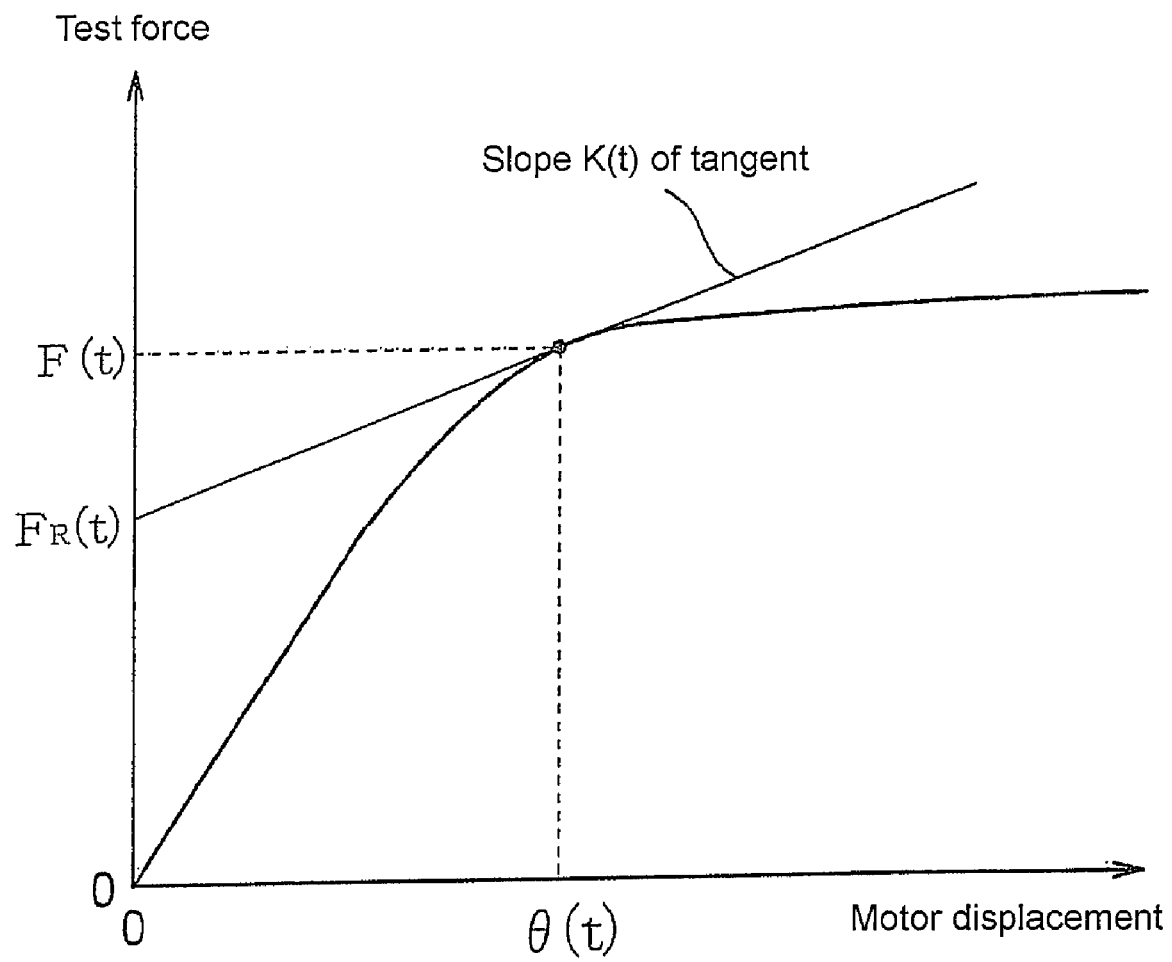
FIG. 2 is a diagram showing a principle of the present invention.

Reference will now be made in detail to the present embodiments of the invention, examples of which are illustrated in the accompanying drawings. Wherever possible, the same reference numbers are used in the drawings and the description to refer to the same or like parts.

The embodiment of the present invention is described below with reference to the accompanying drawings.

FIG. 1 is a structural view of an embodiment of the present invention, a schematic view showing a mechanical configuration, and a block diagram showing an electrical configuration of the present invention.

A testing machine body 1 has the following structure. Two screw rods 12a and 12b are vertically supported on a table 11 in this manner of rotating freely, and nuts (not shown) fixed on two ends of a cross head 13 are screwed into the screw rods 12a and 12b.

On the cross head 13 and the table 11, a pair of chucks 14a and 14b is installed facing each other on the vertical direction, and two ends of a test piece W are held on the chucks 14a and 14b.

The rotation of a servomotor 21 used as a driving source of a loading mechanism 20 is transmitted to the screw rods 12a and 12b through worm reducers 22a and 22b, thereby driving the screw rods 12a and 12b to rotate. The cross head 13 is made to move up and down through the rotation of the screw rods 12a and 12b. When performing a tension test, the cross head 13 is made to rise, so that the test piece W bears a test force (tensile load) F.

The test force applied to the test piece W is inspected by a load sensor 15, and an elongation of the test piece W is inspected by an extensometer 16. Then, the test force and the elongation are respectively amplified by a load amplifier 31 and a strain amplifier 32, and then respectively digitalized by analog-to-digital (A-D) converters 33 and 34, and then input to an operation control unit 30.

The operation control unit 30 includes a computer or a sequencer, and peripheral devices thereof. In each specified short time, the operation control unit 30 obtains the test force data and elongation data from the load sensor 15 and the extensometer 16, and then processes the data, so as to obtain test data for the test force-elongation curve. According to the data set to be the control quantity and the target value of the control quantity in the obtained data, the feedback control is performed on the servomotor 21. In addition, an operating unit 30a is disposed in the operation control unit 30, and the operating unit 30a is operated to send various commands, or set a constant A corresponding to the time constant described as follows.

The servomotor 21 is driven to rotate by a current supplied by the servo amplifier 36. The servo amplifier 36 supplies the current to the servomotor 21, in which the current corresponds to the rotation angle command supplied from the operation control unit 30 and passing through a digital-to-analog (D-A) converter 35.

Furthermore, when the operation control unit 30 sets the test force as the control quantity, the deviation $\{F_D(t)-F(t)\}$ between the inspection value F(t) and the target value $F_D(t)$ of the test force at this time point, and the ratio K(t) of the inspection value F(t) of the test force to the displacement θ(t) of the motor 21 as indicated by Equation (1) are calculated, and the preset constant A is used, so that the rotation angle command dΘH/dt supplied to the servo amplifier 36 is determined through Equation (2), and then the obtained rotation angle command dΘ/dt is supplied to the servo amplifier 36.

The above calculations are performed each time when the test force data is obtained from the load sensor 15, and the data of the inspection value F(t) of the test force and the data of the displacement θ(t) of the motor 21 used in the above calculations at this time point are respectively average values of a plurality of data, for example, approximately 100 data, obtained instantly and stored at this time point. Therefore, even if the data obtained each time include noises, the accurate control is almost not affected by the noises.

According to the above embodiment, the operator does not need to set the control gains by the trial and error as in the prior art, but only needs to set the constant A corresponding to the time constant, so the time is saved. In addition, even those unskilled operators can also perform the setting before test.

Here, in the present invention, besides obtaining the rotation angular velocity command through the Equation (2), an additional item may be added in Equation (2). For example, the following Equation (11) added with a feed forward item is preferably used. In addition, under a situation of adding a velocity feedback item, the following Equation (12) may be used, and under a situation of adding an integral item, the following Equation (13) may be used. In any item, through using K(t), the gains do not need to be set substantially. In addition, B and C in Equations (12) and (13) are constants that may be set at random similar to A.

[Equation 11]

$$\frac{d\Theta(t)}{dt} = \frac{A}{K(t)} \times \{F_D(t) - F(t)\} + \frac{1}{K(t)} \times \frac{dF_D}{dt}. \quad (11)$$

[Equation 12]

$$\frac{A}{K(t)} \times \{F_D(t) - F(t)\} + \frac{C}{K(t)} \times \left\{\frac{F_D(t)}{dt} - \frac{dF(t)}{dt}\right\}. \quad (12)$$

[Equation 13]

$$\frac{A}{K(t)} \times \{F_D(t) - F(t)\} + \frac{B}{K(t)} \times \int \{F_D(t) - F(t)\} dt. \quad (13)$$

Furthermore, in the above embodiment, the situation of selecting the test force as the control quantity is exemplified, but even for the elongation and another physical quantity, K(t) can be instantly calculated in the same manner as described before, and then the value obtained by dividing the deviation by K(t) is taken as the rotation angular velocity of the motor, so as to obtain the same effect as described before.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A material testing machine, for performing a stretching or compression test for a test piece, the material test machine comprising a loading mechanism that applies a load to the test piece; a motor, serving as a driving source of the loading mechanism; a servo amplifier that drives the motor; and a control mechanism sending instantly a rotation angular velocity command of the motor to a servo amplifier, so as to control actions of the loading mechanism, wherein:

the control mechanism is configured to define a rotation angular velocity as a time-vary value and is defined proportional to a ratio of a deviation value to a calculated ratio, the deviation value is a deviation between an inspection value and a target value of a selected control quantity, the calculated ratio is a ratio of the inspection value of the control quantity to a motor displacement, and the control mechanism is further configured to calculate the rotation angular velocity supplied to the servo amplifier as a command.

2. The material testing machine according to claim 1, wherein:

the motor displacement and the inspection value of the control quantity used to calculate the ratio are respectively an average value of a plurality of latest motor displacements and an average value of a plurality of latest inspection values obtained at a time point at which the ratio is calculated.

3. The material testing machine according to claim 1, wherein:

a rotation angle supplied to the servo amplifier is obtained by multiplying a value obtained by dividing the deviation by the ratio with an inverse of a preset time constant.

4. The material testing machine according to claim 2, wherein:

a rotation angle supplied to the servo amplifier is obtained by multiplying a value obtained by dividing the deviation by the ratio with an inverse of a preset time constant.

* * * * *